United States Patent [19]
Dai

[11] Patent Number: 5,847,514
[45] Date of Patent: Dec. 8, 1998

[54] APPARATUS FOR GENERATING NEGATIVE IONS WITH A LID AND A CASING

[76] Inventor: Robert Dai, 5-2Fl., No. 53, Lane 76, Hsueh Fu Rd., Ta Ya Hsiang, Taichung Hsien, Taiwan

[21] Appl. No.: 972,753

[22] Filed: Nov. 18, 1997

[51] Int. Cl.⁶ ................................................. H01T 23/00
[52] U.S. Cl. ................ 315/111.91; 315/58; 315/70; 361/213; 361/230; 361/231; 361/225; 55/385.2; 55/DIG. 5; 96/68; 416/5
[58] Field of Search .................. 315/70, 71, 51, 315/60, 61, 58, 56, 59, 91, 77; 361/225, 230, 231, 213

[56] References Cited

U.S. PATENT DOCUMENTS

| | | | |
|---|---|---|---|
| 4,422,824 | 12/1983 | Eisenhardt, Jr. ............................. | 416/5 |
| 4,596,585 | 6/1986 | Moeller et al. ........................ | 55/385 A |
| 5,189,339 | 2/1993 | Peshak ...................................... | 315/58 |
| 5,241,449 | 8/1993 | Moeller et al. ............................ | 315/70 |
| 5,569,981 | 10/1996 | Cho ............................................ | 315/58 |
| 5,741,352 | 4/1998 | Ford et al. ................................... | 96/68 |
| 5,742,872 | 4/1998 | Copperwheat et al. .................. | 399/92 |

*Primary Examiner*—Don Wong
*Assistant Examiner*—Wilson Lee
*Attorney, Agent, or Firm*—Heller Ehrman White & McAuliffe

[57] ABSTRACT

An apparatus for generating negative ions includes two casings which are coupled each other and respectively have an outer thread on one end thereof, a lid which is fastened to the coupled casings, an electrode rod disposed within the coupled casings, an electrode plate disposed within the coupled casings, a circuit board which is disposed within the combined casings and connected to the electrode rod and the electrode plate and having at least one high voltage discharging plate, a high voltage generator which is connected to the circuit board and the high voltage discharging plate, and a plurality of ventilation slots which are respectively defined in the casings and the lid, such that the apparatus can be easily assembled, installed and utilized as an independent unit.

8 Claims, 6 Drawing Sheets

APPARATUS FOR GENERATING NEGATIVE IONS WITH A LID AND A CASING

BACKGROUND OF THE INVENTION

1. Field of the Invention

The present invention relates to an apparatus for generating negative ions and, in particular, to a negative-ion generating apparatus with a simple structure, easy installation and good air filtering function.

2. Description of the Prior Art

In recent years, more and more people have become concerned about the quality of the air that they breathe. Therefore, numerous kinds of air filtering devices have been developed to meet people's requirements.

One of the widely-used air filtering devices is the negative ion generator. The negative ion generator can collect the air pollutants by negative ions and has the functions of sterilization and purification of air, and activation of oxygen. Furthermore, negative ions can neutralize the excess positive ions in the human body.

However, most conventional negative ion generators are disposed within an air conditioner, a dehumidifier or an air purifier so that a user can not simply use the negative ion generator as an independent unit. In addition, as the dehumidifier and the air purifier are often placed on the ground, the diffusion effect of the negative ions generated thereby is limited.

SUMMARY OF THE INVENTION

Therefore, one purpose of the present invention is to provide an apparatus for generating negative ions, which can be easily assembled, installed and utilized alone.

Another purpose of the present invention is to provide an apparatus for generating negative ions, which can be directly installed in a socket for a light-bulb.

Still another one purpose of the present invention is to provide an apparatus for generating negative ions, which can be directly installed in a socket for a light-bulb on the ceiling or the wall so that the generated negative ions can spread rapidly and evenly.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
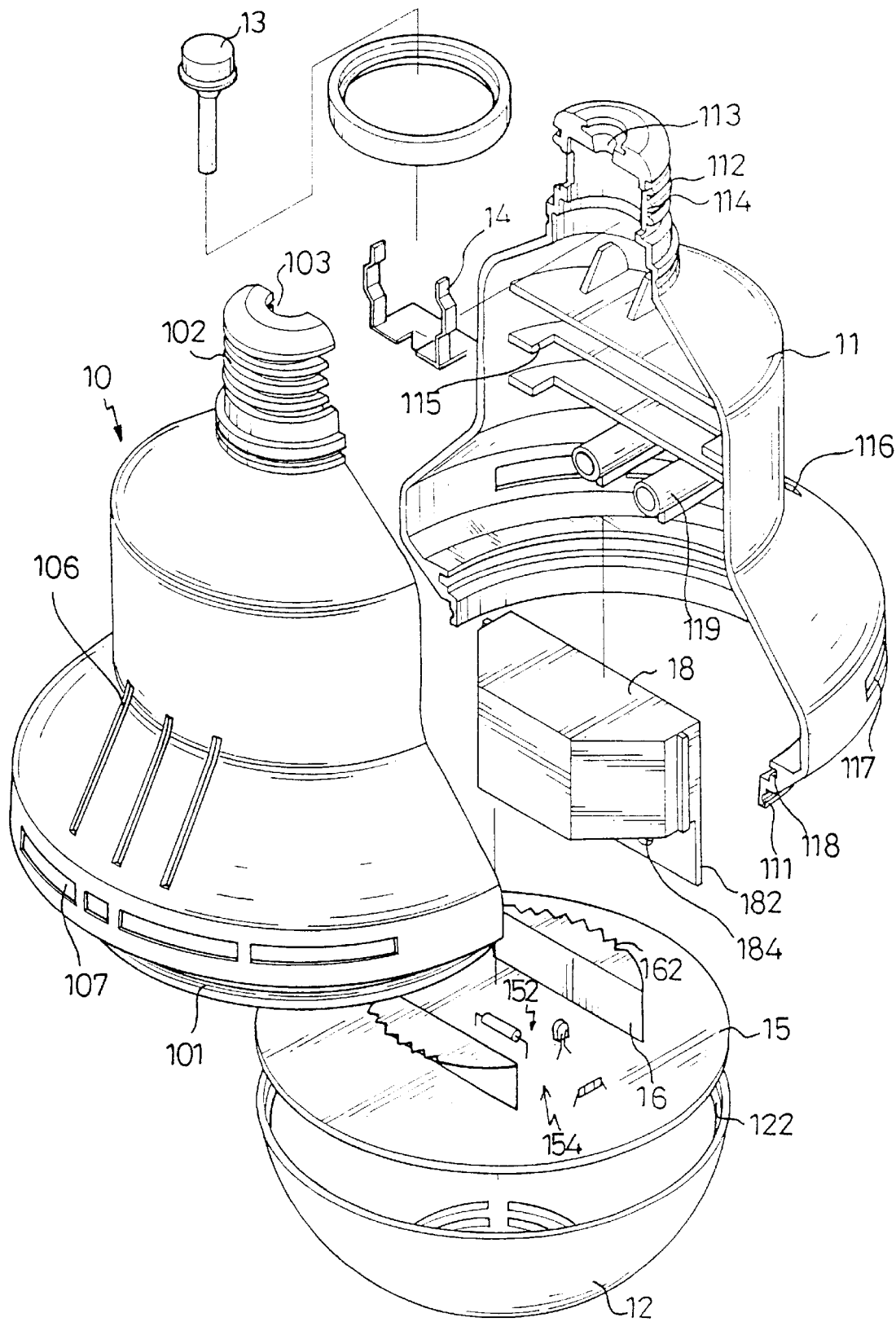
FIG. 1 is an exploded diagram showing the negative ion generator according to the preferred embodiment of the present application.
Figure 2:
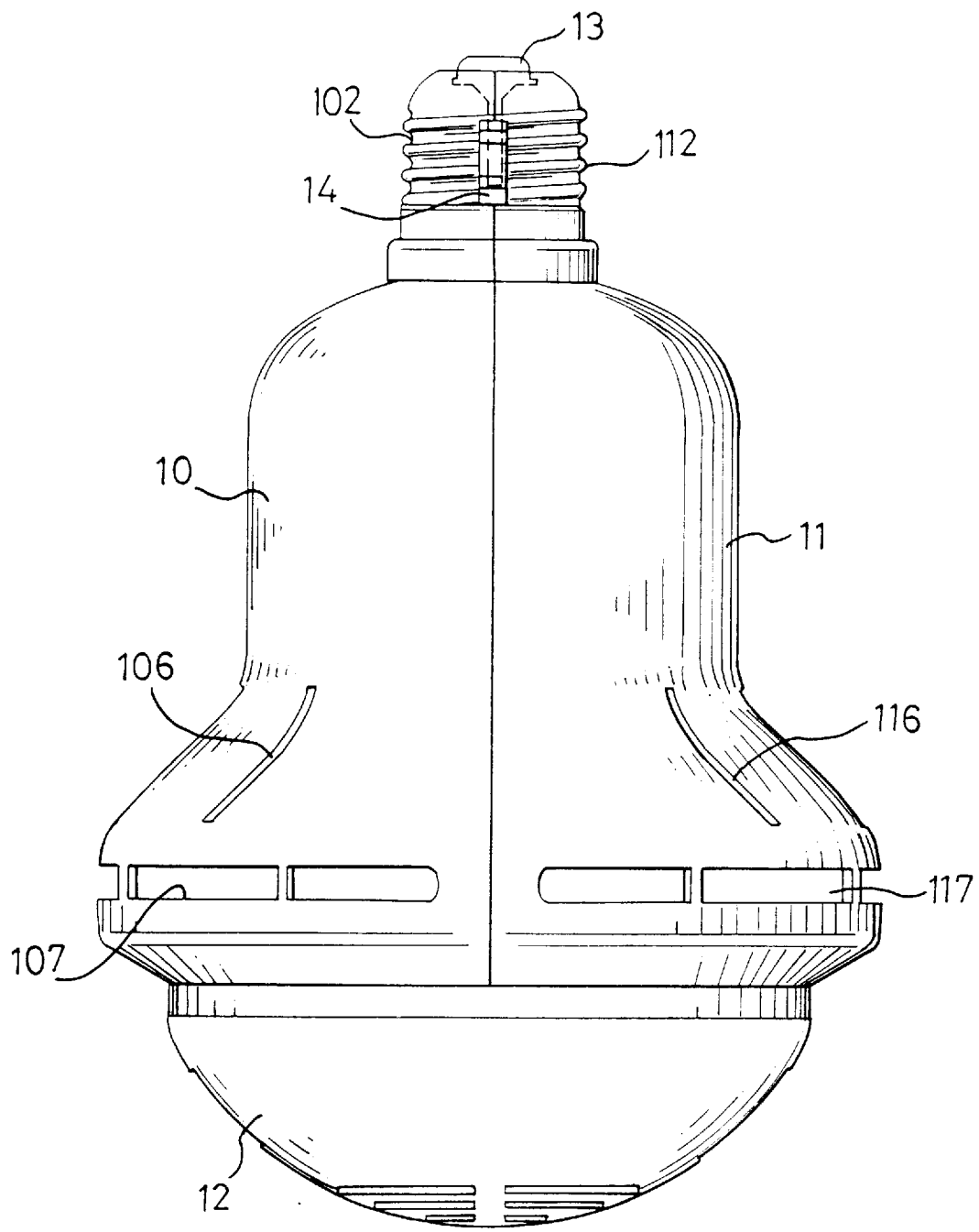
FIG. 2 is an elevational side view of the negative ion generator according to the preferred embodiment of the present application.

According to the preferred embodiment of the present invention, referring to FIGS. 1 and 2, an apparatus for generating negative ions includes two symmetric casings 10, 11 which can be combined to form a single chamber, and a substantially bowl-shaped lid 12 which can be further combined with the two casings 10, 11 to form a complete body. Furthermore, several ventilation slots 106, 107, 116, 117 and 124 are respectively defined in the casings 10, 11 and the lid 12.

Grooves 101, 111 which are respectively defined in an outer periphery of one of two ends of the casings 10, 11, are intended to couple with a protruding ring 122 which is formed on an inner circumference of the lid 12 for fastening the lid 12 to the combined casings 10, 11. The combined casings 10, 11 are further held together by a ring (not numbered) which snugly fits over the second end of the casings 10, 11.

Threaded portions 102, 112, which are respectively formed on the second end of the casings 10, 11, are intended to be used to install the negative ion generating apparatus into a socket, such as a socket commonly used to receive a light-bulb.

A pair of semi-circular openings 103, 113 are respectively defined in a top of the casings 10, 11 to receive an electrode rod 13 therein. A top of the electrode rod 13 protrudes from the top of the combined casings 10, 11 for contacting a first of two electrodes of the socket. Slots 114 are defined in diametrically-opposed positions in the threaded portions 102, 112 of the casings 10, 11 such that a resilient electrode plate 14 which is housed within the casings 10, 11, can protrude from the threaded portions 102, 112 for contacting the other electrode of the socket.

Two linear recesses 108, 118 are respectively defined in inner peripheries of the casings 10, 11 to receive a rim of a circuit board 15 which is electrically connected to the rod 13 and the resilient electrode plate 14. Multiple high voltage discharging plates 16 are disposed on the circuit board 15 and are right-angled in shape with an upright lower portion and an upper portion which has an arcuate free edge 162. The arcuate free edges 162 extend in opposite directions and are serrated. In addition, an overload protection device 152 and a power indicating lamp 154 are fitted to the board 15.

Figure 3:
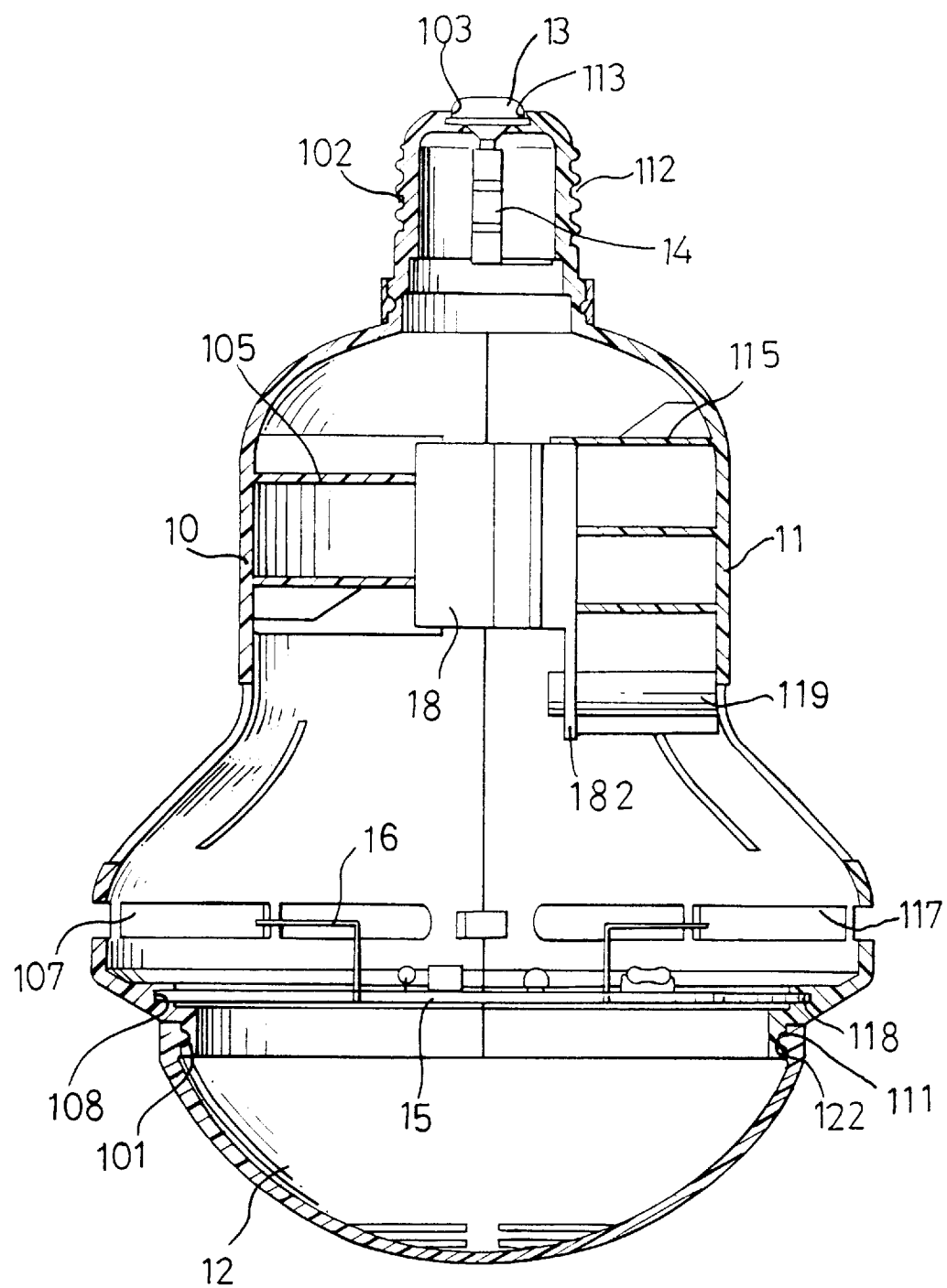
FIG. 3 is a sectional view of the negative ion generator according to the preferred embodiment of the present application.

Referring FIGS. 1 and 3, several clamping plates 105, 115 integrally extend from respective inner faces of a middle portion of the casings 10, 11 for clamping a high voltage generating device 18 which is electrically connected to the plates 16. The high voltage generating device 18 has an assembly plate 182 extending from one end thereof. Multiple assembly holes 184 are defined in the plate 182 for combination with multiple corresponding assembling posts 119 which are formed within the casing 11 in this preferred embodiment, whereby the combination of the high voltage generating device 18 with the casings 10, 11 can be more stable.

Figure 4:
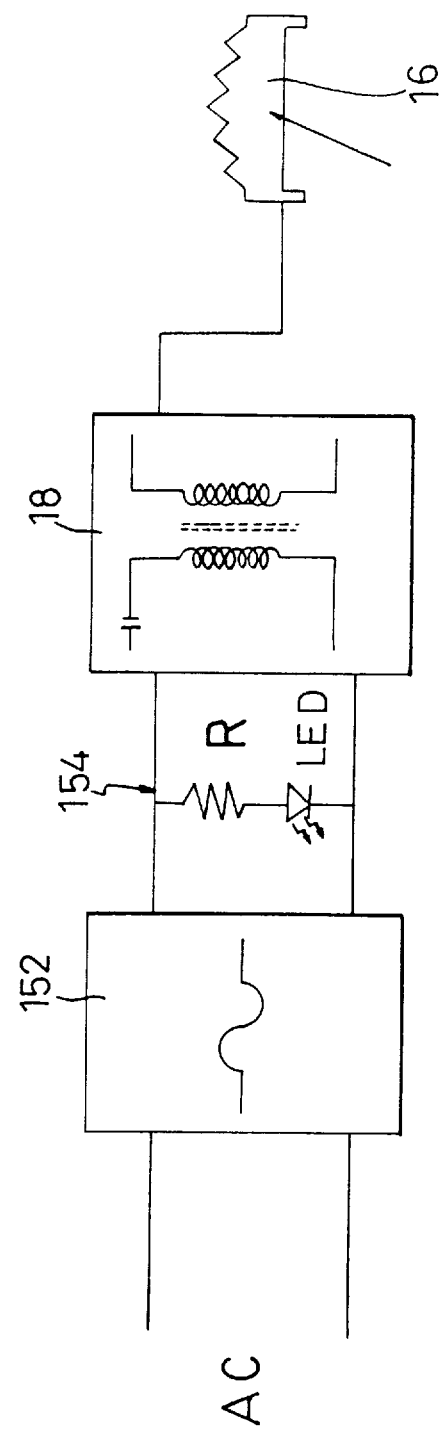
FIG. 4 is a schematic circuit diagram of the negative ion generator according to the preferred embodiment of the present application.

After the negative ion generating apparatus is assembled, it can be threadedly received in the socket, so that power can be supplied to the circuit board 15 and the high voltage generating device 18 inside the apparatus through the electrode rod 13 and resilient electrode plate 14. As shown in FIG. 4, the power is supplied to the high voltage generating device 18 through the overload protection device 152 and the power indicating lamp 154 for generating a high voltage and supply the high voltage to the high voltage discharging plates 16 thereby generating negative ions. The generated negative ions can spread to outside of the casings 10, 11 through the ventilation slots 106, 107, 116, 117 and 124.

Figure 5:
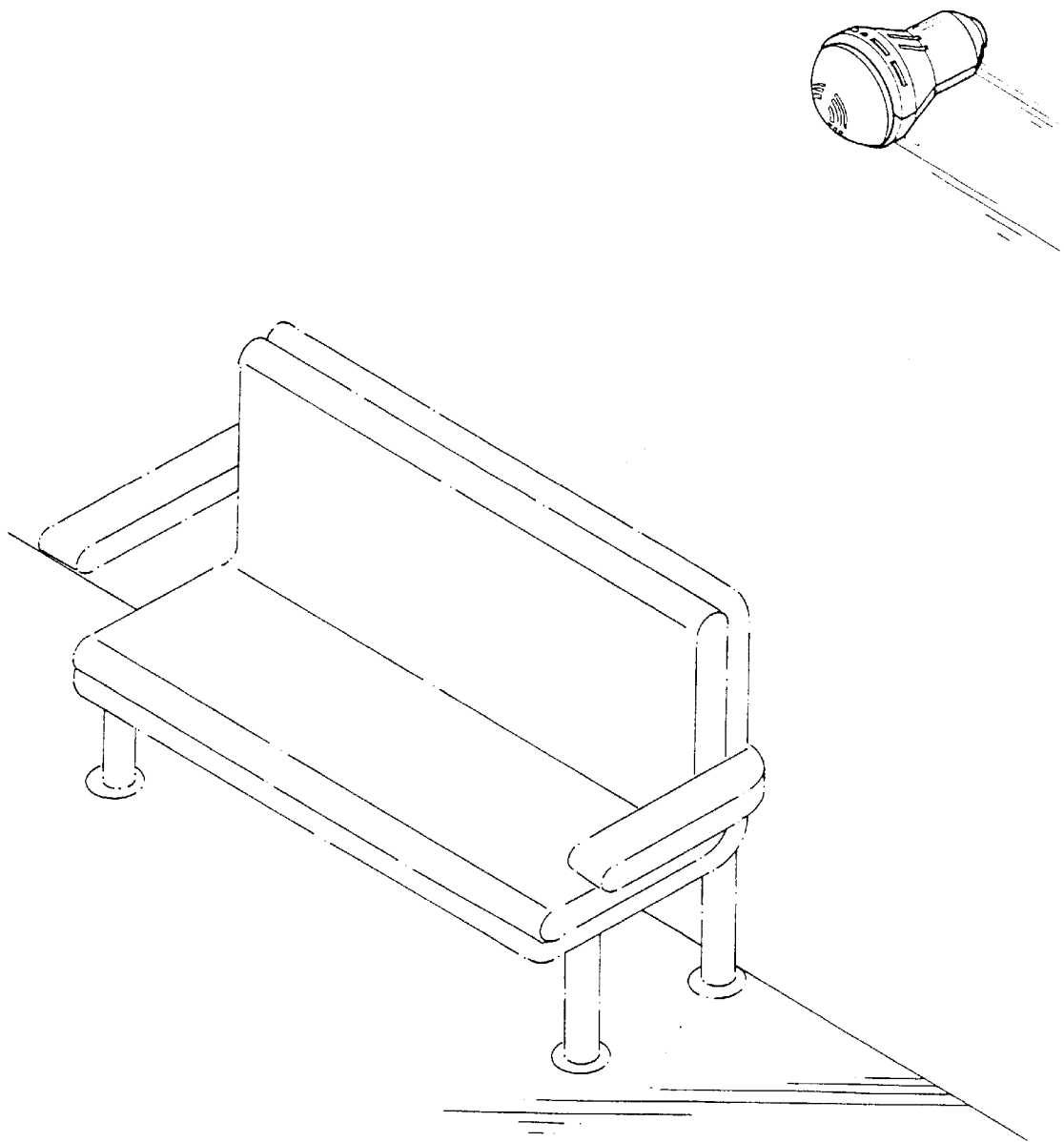
FIG. 5 shows the negative ion generator according to the present application, which is installed on a wall.
Figure 6:
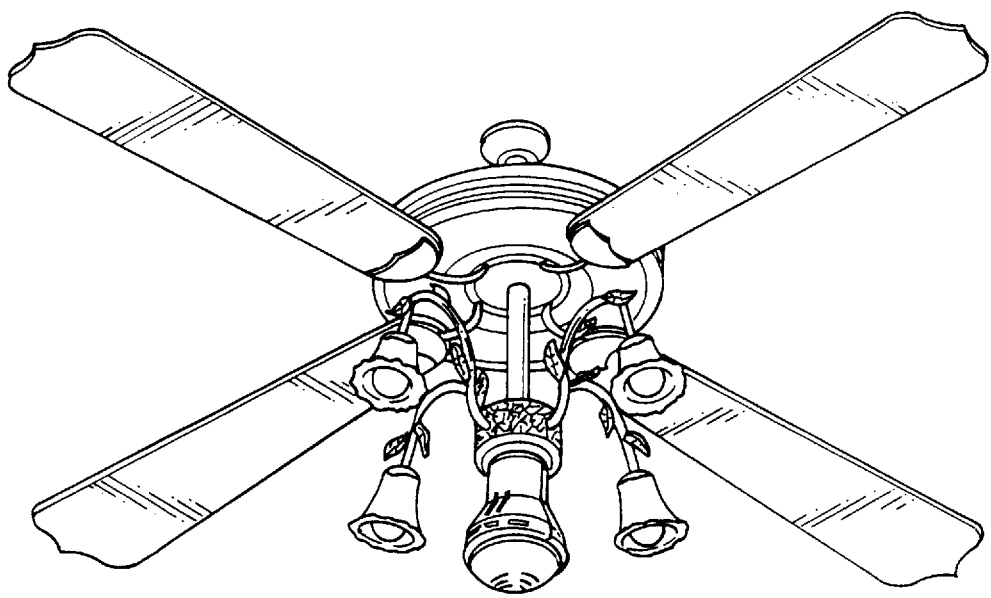
FIG. 6 shows the negative ion generator according to the present application, which is installed on an overhead fan.

As the negative ion generating apparatus of the present application can be directly installed into the socket by using the threaded portions 102, 112 thereof, it is quite easy for a user to install the apparatus. For example, as shown in FIG. 5, the negative ion generating apparatus of the present application can be installed on the ceiling or the wall, so that the apparatus can be disposed at a certain height from the floor. At such disposition, the generated negative ions can diffuse in a manner from top to ground, so that the negative ions can be more evenly distributed in the space of a room. Furthermore, as shown in FIG. 6, the negative ion generating apparatus of the present application can be installed in the socket of a overhead fan such that the effect of the diffusion of generated negative ions can be further promoted due to the operation of the fan.

The present invention mainly utilizes the two casings 10, 11 and the lid 12 to form the body of the negative ion generating apparatus and the threaded portions 102, 112 to allow installation of the apparatus in the socket for a bulb. Therefore, the negative ion generating apparatus of the present application has the advantages of simple structure, convenient assembly and low cost.

While the present invention has been explained in relation to its preferred embodiment, it is to be understood that various modifications thereof will be apparent to those skilled in the art upon reading this specification. For instance, the shapes of the casings 10, 11 and the lid 12 can be changed to match the decoration of a room. Therefore, it is to be understood that the invention disclosed herein is intended to cover all such modifications as falling within the scope of the appended claims.

I claim:

1. An apparatus for generating negative ions comprising:

two casings, which are coupled each other, respectively having an outer threaded portion on a first end thereof;

a lid which is fastened to the coupled casings;

an electrode rod disposed within the coupled casings, an end of which protrudes from the first end of the coupled casings;

an electrode plate disposed within the coupled casings, a portion of which protrudes from the two threads;

a circuit board, which is disposed within the combined casings and connected to the electrode rod and the electrode plate, having at least one high voltage discharging plate;

a high voltage generator which is connected to the circuit board and the high voltage discharging plate; and a plurality of ventilation slots which are respectively defined in the casings and the lid.

2. An apparatus for generating negative ions of claim 1, further comprising two openings respectively defined in the first end of the casings and at least one slot defined in a circumference of the coupled casings to accommodate the electrode plate which protrudes from the threaded portions.

3. An apparatus for generating negative ions of claim 1, further comprising at least one recess defined formed inside the coupled casings for holding the circuit board.

4. An apparatus for generating negative ions of claim 1, further comprising a plurality of plates disposed inside the coupled casings for clamping the high voltage generator.

5. An apparatus for generating negative ions of claim 1, wherein the circuit board comprises an overload protection device.

6. An apparatus for generating negative ions of claim 1, wherein the circuit board comprises a power indicating lamp.

7. An apparatus for generating negative ions of claim 1, wherein the high voltage generator includes an assembly plate extending from one end thereof, at least one hole being developed on the assembling plate, and at least one corresponding post is formed inside the casings for co-operating with said at least one hole.

8. An apparatus for generating negative ions of claim 1, wherein the high voltage discharging plate includes a serrated edge.

\* \* \* \* \*